United States Patent [19]

Nocca et al.

[11] Patent Number: 4,847,431
[45] Date of Patent: Jul. 11, 1989

[54] PROCESS FOR MANUFACTURING A TERTIARY ALKYL ETHER BY REACTIVE DISTILLATION

[75] Inventors: Jean-Luc Nocca, Rueil-Malmaison; Jacques Leonard, Montigny; Jean-Ferdinand Gaillard, Lyons; Pierre Amigues, Francheville, all of France

[73] Assignees: Institut Francais du Petrole, Rueil-Malmaison; Elf France, Courbevoie, both of France

[21] Appl. No.: 171,340

[22] Filed: Mar. 21, 1988

[51] Int. Cl.$^4$ ............................................. C07C 41/06
[52] U.S. Cl. ............................. 568/197; 203/DIG. 6; 202/158; 422/193
[58] Field of Search .................. 568/697; 203/DIG. 6

[56] References Cited

U.S. PATENT DOCUMENTS

| | | | |
|---|---|---|---|
| 3,629,478 | 12/1971 | Haunschild | 568/697 X |
| 4,232,177 | 11/1980 | Smith | 568/697 X |
| 4,439,350 | 3/1984 | Jones | 568/697 X |

Primary Examiner—Howard T. Mars
Attorney, Agent, or Firm—Millen, White & Zelano

[57] ABSTRACT

Process for manufacturing methyl tert-butyl ether (MTBE) by reacting methanol with isobutene-containing hydrocarbons in a reaction zone comprising alternate beds of sulfonated resin catalyst and catalyst-free distillation zones, said zones also comprising liquid redistribution plates.

10 Claims, 1 Drawing Sheet

PROCESS FOR MANUFACTURING A TERTIARY ALKYL ETHER BY REACTIVE DISTILLATION

The present invention concerns a process for manufacturing a tertiary alkyl ether by reacting an aliphatic alcohol with a hydrocarbon mixture containing at least one iso-olefin.

It also concerns an apparatus for carrying out said process.

The present invention more particularly concerns the manufacture of methyl tert-butyl ether (MTBE) from isobutene and methanol, the manufacture of tert-amyl methyl ether (TAME) from isopentene and methanol and the manufacture of MTBE and TAME from isobutene, isopentene and methanol.

BACKGROUND OF THE INVENTION

Tertiary alkyl ethers, particularly methyl tert-butyl ether (MTBE) and tert-amyl methyl ether (TAME) are of high interest for improving the gasoline qualities.

Thus, the use of methyl tert-butyl ether (MTBE), in view of its antiknock properties, improves the quality of commercial gasolines, resulting in a higher octane number than that obtained by addition of methanol, one of the best additives. In addition, methyl tert-butyl ether (MTBE) has a calorific value higher than that of methanol: 8,395 kcal/kg (35,091 kJoule/kg) for MTBE, as compared with 4,764 kcal/kg (19,914 kJoule/kg) for methanol (as an average the calorific value of a primium gasoline is 10,200 kcal/kg, i.e. 42,636 kJoule/kg). Moreover, the use of MTBE does not result in demixion difficulties in the presence of water, as for methanol. Finally, the solubility in water of MTBE being considerably higher than that of water in hydrocarbons, the addition of MTBE improves the tolerance to water of motor-fuels.

It is known to prepare tertiary alkyl ethers, particularly methyl tert-butyl ether (MTBE) and tert-amyl methyl ether (TAME) which are the most conventional ethers, by reacting an iso-olefin, generally contained in a hydrocarbon fraction, with an alcohol, for example methanol, in the presence of an acid catalyst, for example sulfuric acid, hydrofluoric acid, aluminum chloride or boron fluoride, or in the presence of carbonaceous materials containing —$SO_3H$ groups, for example sulfonated coals, sulfonated phenol-formaldehyde resins, sulfonated coumarone-indene polymers or preferably sulfonated polystyrene-divinylbenzene resins.

It has been known for a long time that the reaction between methanol and tertiary olefins is a balanced reaction and there fore it is difficult to obtain high conversion rates. The equilibrium is less displaced in favor of ether formation that the molecular weight of the iso-olefin is higher. Thus, for iso-amylenes, the conversion rate is limited to 65–75% when the use of a too large methanol excess is to be avoided. To obtain acceptable conversion rates of iso-olefins, particularly of iso-amylenes, a very large methanol excess with respect to the stoichiometry must be used. Consequently, the methanol amount contained in the reaction mixture is too large to be easily removed in a conventional manner, such as by azeotropic distillation with hydrocarbons and recycling to the reactor, as disclosed in the French Pat. No. 2 411 811. According to U.S. Pat. No. 4,204,077, methanol could then be removed by extraction with a solvent such as ethylene glycol.

In these conventional techniques, the tertiary alkyl ether formed by reaction of an alcohol with an iso-olefin contained in a hydrocarbon mixture, is obtained within a mixture of unconverted hydrocarbons and occasionally of unconverted alcohol. After completion of the etherification reaction, generally in at least two reactors, the tertiary alkyl ether must be separated from the other constituents in several distillation columns, while simultaneously removing the maximum alcohol amount with the minimum loss of ether.

Thus, the use of several reactors and distillation columns for manufacturing and separating the tertiary alkyl ether increases the investment and operating costs without giving a high ether yield.

A method has been proposed for solving the relevant problems: it involves the reactive distillation (or catalytic distillation), in which the etherification reaction with a catalyst and the distillation for separating the tertiary alkyl ether, as it is formed, from the other unconverted constituents are performed in the same enclosure (U.S. Pat. No. 3,629,478, EP-B 8 860, FR 2 503 700).

According to U.S. Pat. No. 3,629,478, the catalyst is placed in bulk in discharge gutters (or downcomers) of distillation sieve trays: according to this patent only the descending liquid phase is in contact with the catalyst, the vapor phase rising through the perforations of each distillation tray. In fact, due to the reaction exothermicity, the formation of a vapor phase at contact with the catalyst is unavoidable and gives rise to a hydrodynamic problem: as a matter of fact, it will be very difficult, if not impossible, for a mixed phase consisting of the liquid plus the vapor formed by the reaction heat, i.e a light phase, to descend through the discharge gutters, in view of the high resistance to its passage due to the small section of said gutters and to the catalyst contained therein.

The European Pat. No. 8 860 proposes to feed with an isobutene and methanol-containing mixture a distillation column filled with a catalyst convenient for producing methyl tert-butyl ether (MTBE), wherein the catalyst also acts as packing for the distillation, thus forming MTBE and simultaneously separating $C_4$ constituents.

Although the process disclosed in this patent already represents an important technical progress in the field of reactive distillation, it is further substantiallly improved according to the invention, as a result, in particular, of a more important distillation operation.

French Pat. No. 2 503 700 proposes the use of a series of catalytic steps with ascending vapor-liquid flow through each catalyst bed, with the catalyst being embedded. But the distillation effect is not as important as expected. Moreover, a hydrodynamic problem may arise: as a matter of fact, in view of the gravity effect, it is not easy for the fluid to flow upwardly through each catalyst bed.

SUMMARY OF THE INVENTION

The present invention copes with the above-mentioned disadvantages by simultaneously performing in the same single enclosure, in the presence of a suitable catalyst, the reaction producing the tertiary alkyl ether and the separation of the latter, by distillation, from the accompanying hydrocarbons and compounds, while obtaining very satisfactory yields to ether, mainly as a result of a very good distillation effect.

BRIEF DESCRIPTION OF THE DRAWINGS

The invention will be now described more in detail by way of illustrative and non-limiting examples, with reference to the accompanying drawings, wherein.

Figure 2:
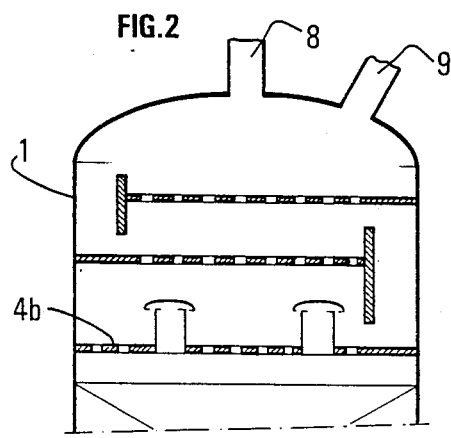
Figure 3:
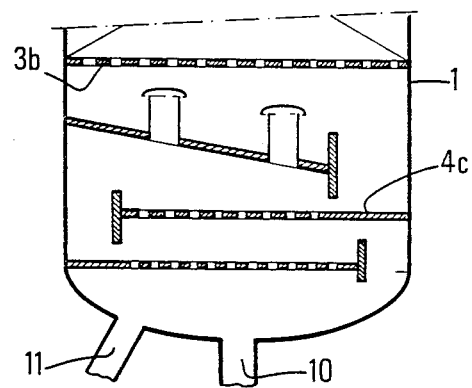

The present invention has for object a process for manufacturing one or more tertiary alkyl ether(s), by reacting an aliphatic alcohol with a hydrocarbon mixture containing at least one iso-olefin, in a reaction-distillation zone (where the reaction and/or the distillation are performed) defined (see FIGS. 1, 2 and 3) by an enclosure (1) of substantially cylindrical shape, for example vertical, containing at least one catalyst of the sulfonated resin type, for example a sulfonated polystyrene-divinylbenzene resin, said process being characterized by the steps of:

(i) introducing the charge of reactants, comprising at least said alcohol and at least said hydrocarbon mixture, into said reaction-distillation zone which contains:

(a) at least two superposed and non-contiguous fixed beds (2a, 2b) of said catalyst of sulfonated resin type, each of said beds being placed on a perforated support member or base plate (3a, 3b) (which may be for example a perforated disc, a supporting grid or a net) and comprising a plurality of fabric pockets containing said catalyst, said pockets leaving free spaces therebetween, said catalyst beds being optionally of different thicknesses, (b) at least one catalyst-free distillation zone in at least one free space between two consecutive catalyst beds (2a, 2b), (c) at least one catalyst-free discontinuous tray (5) (i.e provided with a plurality of discontinuities) for liquid redistribution, located in at least one free space between a distillation zone and the catalyst bed just below said distillation zone, (ii) maintaining the distillation conditions in said reaction-distillation zone, so as to obtain a descending liquid phase and an ascending vapor phase in said zone, (iii) discharging from the top (8) of the reaction-distillation zone a vapor phase mainly containing unconverted hydrocarbons and, (iv) withdrawing from the bottom (10) of the reaction-distillation zone a liquid phase mainly containing said tertiary alkyl ether(s).

The term distillation zone is used to designate any device known in the art for performing a distillation, such as:

at least one inert packing with a support member, and/or at least one discontinuous distillation tray (4a) (i.e a tray provided with discontinuities for giving passage to the vapor phase, and with at least one discharge duct (or downcomer) edged with an overflow for the liquid phase), mainly selected from the following type:
sieve trays,
valve trays,
bubble-cap trays.

Each liquid redistribution tray (5) is provided with a plurality of discontinuities. At least one of aid discontinuities consists of a funnel or duct for the passage of the vapor phase, the upper end part of which is preferably protruding, i.e raises above the bottom of said liquid redistribution tray (5), said end being preferably covered (but not closed), thus preventing the liquid present on said tray from being discharged through said funnel or duct. Other discontinuities of said tray are orifices for the passage of the liquid phase, these orifices being so distributed as to make possible a uniform spraying with liquid phase of the catalyst bed just below each liquid redistribution tray.

In each of the catalyst beds, the free space around the fabric pockets containing the catalyst (said pockets being permeable to liquid but impermeable to solid catalyst particles) give free passage to liquid and vapor, hence with a certain distillation effect, substantially improved by the presence of one or more distillation zones.

Advantageously, at least a part of the vapor phase discharged from the top (8) of the reaction-distillation zone may be condensed (in a condenser external to the enclosure (1) defining said zone, not shown in the figures), then fed back to said zone, for example to the top thereof (line 9), as liquid flow, called reflux.

Similarly, at least a part of the liquid phase withdrawn from the bottom of the reaction-distillation zone through line (10) may be vaporized (by passage through a reboiler external to enclosure 1, not shown in the figures) and then reintroduced into said zone, for example at the bottom part thereof, through line (11), as vapor flow, called reboiling vapor.

According to a preferred embodiment of the invention (see FIG. 1) where at least one distillation zone comprises one or more distillation trays, the liquid phase is supplied onto each distillation tray just below a catalyst bed, at the most remote place from the overflow thereof, i.e at the opposite of said overflow, after previous passage over a catalyst-free liquid distribution tray (6), traversed by at least one duct or funnel for the passage of the vapor phase (duct or funnel whose upper end is preferably protruding above the tray bottom, said upper end being provided with a cap for preventing the liquid flow passage through said duct or funnel), substantially inclined, located in each free space between a distillation tray and the catalyst bed just above said tray, each liquid distribution tray (6) being further provided, at its lowermost end, with a free passage-way (preferably consisting of a discharge gutter or duct edged with a small lip) for the liquid phase: the liquid downward flow from the distillation tray is thus more regular and the distillation on said tray still more efficient.

The space between the top of the reaction-distillation zone (i.e the top of the enclosure) and the uppermost catalyst bed of said zone (see FIG. 2) may preferably contain a catalyst-free distillation zone (for example, at least one discontinuous distillation tray 4b).

The space between the bottom of the reaction-distillation zone (the bottom of the enclosure) and the lowermost catalyst bed of said zone (see FIG. 3), may also preferably contain a catalyst-free distillation zone (for example at least one discontinuous distillation tray 4c).

According to another preferred embodiment of the invention (see FIG. 1), the charge of reactants, containing at least one aliphatic alcohol and at least one hydrocarbon mixture, is introduced into the reaction-distillation zone at a level (7) thereof below at least one catalyst bed and more preferably such that the lowerr most catalyst bed of said zone be above said level.

It is optionally possible, in addition to the charge, to introduce said alcohol separately (i.e alone) into the reaction-distillation zone, through at least one inlet port different from that of said charge and preferably located in the vicinity of the top of said reaction-distillation zone (for example above the uppermost catalyst bed of said zone and preferentially below the reflux feeding port).

This additional alcohol amount favors the etherification reaction and results in a higher conversion rate of the iso-olefin. Moreover, it has the effect of reducing the eventual formation of dimers. The alcohol is preferably injected at a temperature lower than its boiling temperature.

According to another embodiment of the invention, the fabric pockets containing the catalyst may be fastened to grids which are rolled up on themselves and superposed on each other and whose meshes are in major part metallic (each catalyst bed thus comprising at least one layer of said grids).

The reflux ratio (i.e a ratio between the reflux liquid and the withdrawn liquid), in proportion to the distillate, is generally maintained in the range from 0.1:1 to 20:1, preferably from 0.5:1 to 10:1. The operation is mostly conducted inside enclosure (1) within a relatively wide pressure and temperature range: for example a pressure of 1–30 bars (100–3,000 kPa), preferably 2–20 bars (200–2,000 kPa) and a temperature from 10 to 200° C., preferably from 40° to 160° C., in the whole enclosure.

Each of the catalyst beds used according to the invention fills the whole circular section of the reaction-distillation zone, i.e the whole circular section of the enclosure (1).

Figure 1:
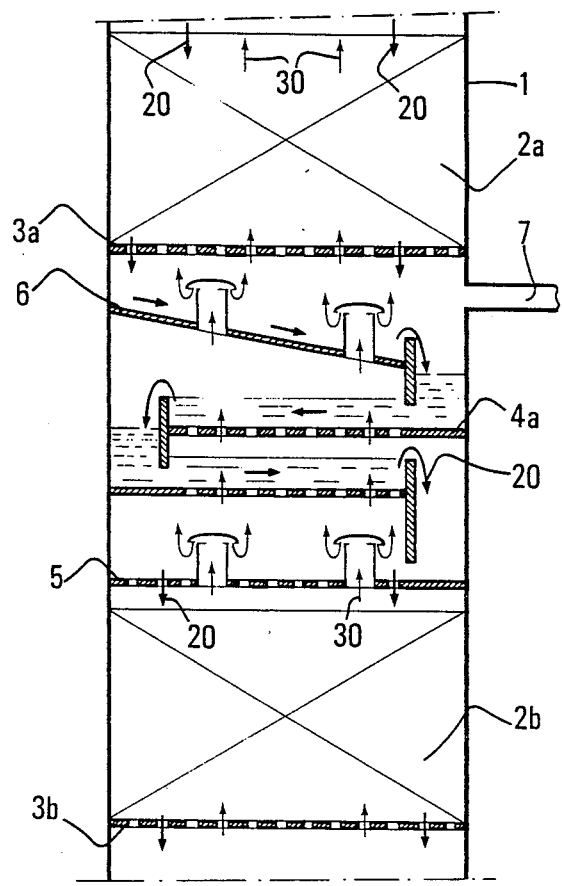
FIGS. 1, 2 and 3 illustrate the enclosure according to the invention, FIG. 1 being a view of the middle part of the enclosure, FIGS. 2 and 3 being respectively longitudinal cross-sectional views of the upper part and of the bottom part of the enclosure.

In FIG. 1, given by way of example, the liquid phase preferentially follows the path indicated by arrows 20 and the vapor phase preferentially follows the path indicated by arrows 30.

As it flows downwardly through the reaction-distillation zone, the liquid phase progressively increases its content of tertiary alkyl ether, which is less volatile than the alcohol and the still unreacted iso-olefin, and than the other non etherifiable constituents of the hydrocarbon mixture which, in contrast to the tertiary alkyl ether, tend to flow upwardly towards the top of the reaction-distillation zone. Thus the liquid phase withdrawn at the bottom of said zone mainly contains tertiary alkyl ether. Moreover, the vapor phase discharged from the top of said zone is generally free of unconverted alcohol, except as traces.

The present invention has also for object (see FIGS. 1, 2 and 3) an apparatus or vessel (1) substantially of cylindrical shape, comprising at least one line (7) for introducing a charge, at least one line (8), at the top of said vessel, for withdrawing a vapor phase, at least one line (9), in the vicinity of the top of said vessel, for a reflux feed, at least one line (10), at the bottom of said vessel, for withdrawing a liquid phase, at least one line (11) for introducing an at least partly vaporized phase, said vessel being characterized in that it contains:

(a) at least two superposed and non-contiguous fixed catalyst beds (2a, 2b), each of said beds being placed on a perforated support member of bottom (3a, 3b) (consisting for example of a perforated disc, a supporting grid or a net), filling the whole internal circular section of vessel (1), (b) at least one distillation device, located in at least one free space between two consecutive catalyst beds (2a, 2b), and (c) at least one discontinuous tray (5) (provided with a plurality of discontinuities such for example as ducts or funnels whose upper end may be protruding and covered), for liquid redistribution, located in at least one free space between a distillation apparatus and the catalyst bed just below it.

By distillation apparatus, it is meant any apparatus known in the art for performing a distillation, such as:
at least one inert packing provided with a support member, and/or
at least one discontinuous distillation tray (4a) (i.e provided with discontinuities for the passage of the vapor phase and with at least one discharge duct (or downcomer) edged with an overflow for the liquid phase) mainly selected from the following types:
sieve trays,
valve trays,
bubble-cap trays.

The apparatus (1) according to the invention may further comprise, when at least one distillation device is formed of one or more distillation trays, at least one liquid distribution tray (6), wherethrough passes at least one duct or funnel (whose upper end is preferably protruding and provided with a cover), substantially inclined, located in at least one free space between a distillation tray and the catalyst bed just above it, each liquid distribution tray being provided at its lowermost end with at least one free passage-way (preferably consisting of a discharge gutter or duct edged with an overflow).

The vessel (1) according to the invention may also contain at least one device selected from the following group of:
at least one distillation device between the top of the vessel and the uppermost bed therein, and
at least one distillation device between the bottom of the vessel and the lowermost catalyst bed therein.

This apparatus is adapted for carrying out the process according to the invention.

The apparatus may be used, for example, for manufacturing methyl tert-butyl ether (MTBE) from methanol and isobutene, for manufacturing tert-amyl methyl ether (TAME) from methanol and isopentene and manufacturing MTBE or TAME from methanol, isobutene and isopentene, in the presence of a convenient catalyst such as a catalyst of sulfonated resin type (for example a sulfonated polystyrene-divinylbenzene resin), these types of use being not limitative.

EXAMPLE (comparative)

A charge, formed of methanol and of a mixture of butenes and butanes containing about 25% of isobutene, already converted to MTBE in a proportion of 80% over a bed of sulfonated resin catalyst, is introduced into an enclosure containing a plurality of beds of said catalyst and of distillation trays: according to the process of the invention (operating pressure of about 10 bars, temperature ranging from about 60° to 135° C. and reflux ratio of about 1:1) about 80% of the residual isobutene may then be converted to MTBE in said enclosure, in particular by placing a distillation tray in each space available between two consecutive catalyst beds. It is observed that, for the same results, the number of said catalyst beds used in the process of the invention is one half of the number of such beds required in a conventional catalytic column.

What is claimed as the invention is:

1. A process for manufacturing a tertiary alkyl ether by reacting an aliphatic alcohol with a hydrocarbon mixture containing at least one iso-olefin, in a reaction-distillation zone defined by an enclosure of substantially cylindrical shape, containing at least one catalyst of the sulfonated resin type, characterized by the steps of:
  (i) introducing the reactant charge containing at least said alcohol and at least said hydrocarbon mixture into said reaction-distillation zone, which contains:
    (a) at least two superposed and non-contiguous fixed beds of said catalyst of sulfonated resin type, each of said beds being placed on a perforated support member and comprising a plurality of fabric pockets containing said catalyst, free spaces being provided between said pockets,
    (b) at least one catalyst-free distillation zone, located in at least one free space between two consecutive catalyst beds,
    (c) at least one catalyst-free discontinuous tray for liquid redistribution, located in at least one free space between a distillation zone and the catalyst bed just below said distillation zone, wherein each discontinuous liquid redistribution tray is provided with at least one funnel or duct through which a vapor phase passes,
  (ii) maintaining distillation conditions in the reaction-distillaton zone, so as to have a descending liquid phase and an ascending vapor phase in said zone,
  (iii) discharging from the top of the reaction-distillation zone a vapor phase mainly containing unconverted hydrocarbons, and
  (iv) withdrawing from the bottom (10) of the reaction-distillation zone a liquid phase mainly containing said tertiary alkyl ether.

2. A process according to claim 1, wherein at least a part of the vapor phase discharged at the top of the reaction-distillation zone is condensed and then fed back to said zone as liquid flow.

3. A process according to claim 1, wherein at least a part of the liquid phase withdrawn from the bottom of the reaction-distillation zone is vaporized and then reintroduced into said zone as vapor flow.

4. A process according to claim 1, wherein the space between the top of the reaction-distillation zone and the uppermost catalyst bed of said zone contains a catalyst-free distillation zone.

5. A process according to claim 1, wherein the space between the bottom of the reaction-distillation zone and the lowermost catalyst bed of said zone contains a catalyst-free distillation zone.

6. A process according to claim 1, wherein at least one distillation zone comprises at least one discontinuous distillation tray.

7. A process according to claim 6, wherein the liquid phase is supplied to each distillation tray just below a catalyst bed, on the side opposite to the overflow of said distillation tray, after previous passage over a catalyst-free liquid distribution tray, wherethrough passes at least one duct for the vapor phase, substantially inclined, placed in each free space between a distillation tray and the catalyst bed just above said distillation tray, each liquid distribution tray being provided at its lowermost end with at lest one free passage-way for the liquid phase.

8. A process according to claim 1, characterized in that the reactant charge containing at least said alcohol and at least said hydrocarbon mixture is introduced into the reaction-distillation zone at such a level that at least one catalyst bed is above said position.

9. A process according to claim 1, characterized by further introducing alcohol of said type, in addition to the charge, separately into the reaction-distillation zone, through at least one port different from that used for introducing said charge, located in the vicinity of the top of said zone.

10. A process according to claim 1, wherein the aliphatic alcohol is methanol and the iso-olefin is selected from the group consisting of isobutene, isopentene and a mixture of isobutene with isopentene.

* * * * *